United States Patent
Shrikhande et al.

(10) Patent No.: US 12,036,398 B1
(45) Date of Patent: Jul. 16, 2024

(54) TREATMENT OF NEUROMUSCULAR DYSFUNCTION

(71) Applicant: Pelvic Rehabilitation Medicine, West Palm Beach, FL (US)

(72) Inventors: Allyson A. Shrikhande, Palm Beach, FL (US); Gautam V. Shrikhande, Palm Beach, FL (US)

(73) Assignee: Pelvic Rehabilitation Medicine, West Palm Beach, FL (US)

( * ) Notice: Subject to any disclaimer, the term of this patent is extended or adjusted under 35 U.S.C. 154(b) by 0 days.

(21) Appl. No.: 18/394,510

(22) Filed: Dec. 22, 2023

(51) Int. Cl.
- *A61M 5/42* (2006.01)
- *A61K 9/00* (2006.01)
- *A61K 31/167* (2006.01)
- *A61K 31/573* (2006.01)

(52) U.S. Cl.
CPC ........... *A61M 5/427* (2013.01); *A61K 9/0019* (2013.01); *A61K 31/167* (2013.01); *A61K 31/573* (2013.01)

(58) Field of Classification Search
CPC ... A61M 5/427; A61K 9/0019; A61K 31/167; A61K 31/573
See application file for complete search history.

(56) References Cited

U.S. PATENT DOCUMENTS

| | | | |
|---|---|---|---|
| 2001/0025057 A1* | 9/2001 | Gorfine | A61P 25/04 514/742 |
| 2007/0255333 A1* | 11/2007 | Giftakis | A61N 1/36071 607/46 |
| 2014/0243657 A1* | 8/2014 | Maizes | A61B 8/0841 600/424 |
| 2014/0324072 A1* | 10/2014 | Harari | A61F 2/0063 606/139 |
| 2020/0197567 A1* | 6/2020 | Christman | A61L 27/58 |
| 2022/0015738 A1* | 1/2022 | Harbi | A61P 23/02 |

FOREIGN PATENT DOCUMENTS

WO WO-2013153496 A1 * 10/2013 ........... A61K 31/137

* cited by examiner

*Primary Examiner* — Lauren P Farrar
(74) *Attorney, Agent, or Firm* — Blank Rome LLP

(57) ABSTRACT

Neuromuscular disfunction in patients with chronic pelvic pain can be treated with anesthetic injections to the levator ani sling muscles (to reduce muscle spasticity) and high volume pudendal and posterior femoral cutaneous nerve blocks (to both reduce neurogenic inflammation and mechanically open the space so the nerves can flow freely with less restriction and more blood flow). Additionally, to treat the peripheral and central sensitization found in chronic pelvic pain patients, embodiments of the disclosed treatment include high volume nerve blocks of the ilioinguinal, genitofemoral, pudendal, and/or perineal nerves.

30 Claims, 1 Drawing Sheet

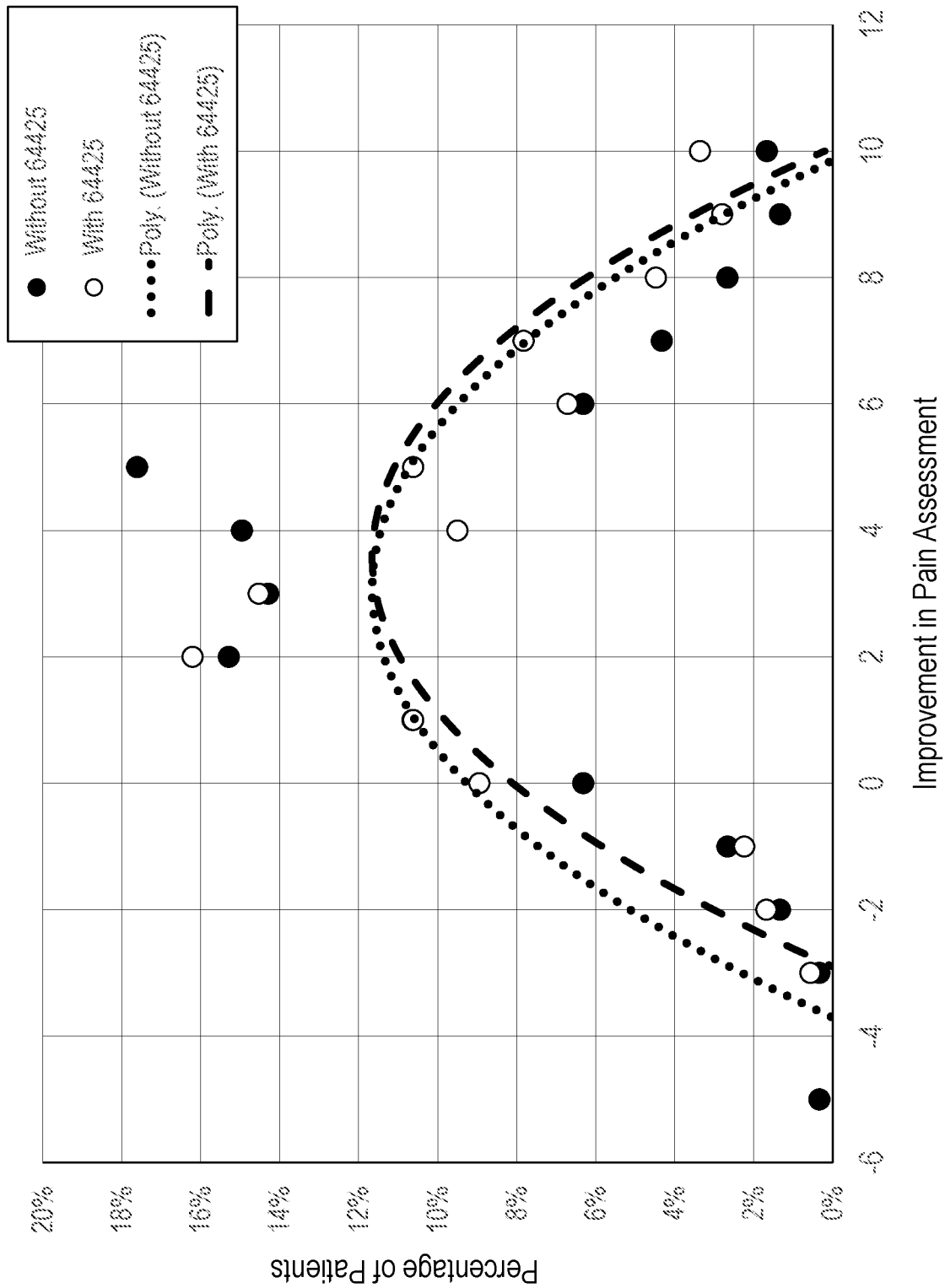

TREATMENT OF NEUROMUSCULAR DYSFUNCTION

BACKGROUND

Chronic Pelvic Pain (CPP) affects 15 percent of women and 8-10 percent of men. CPP is characterized by noncyclical pain in the pelvis or abdomen present for 3-6 months, interfering with daily function. Rather than being perceived as a single disorder, CPP should be viewed as a pattern of symptoms caused by overlapping conditions, including Interstitial Cystitis (IC)/Bladder Pain Syndrome (BPS), Endometriosis, Irritable Bowel Syndrome (IBS), and Pelvic Myofascial Pain. This prevalence between CPP and disorders of the urological organs, reproductive tract, gastrointestinal system, and musculoskeletal system explains the uncertainty in CPP's etiology.

Treatment of CPP may consist of treatment of chronic pain as a diagnosis and/or treatment of the disorders that might be a cause of or contributor to CPP. The best treatment option for this minimally understood pain complex is uncertain. Current pharmacological treatments in CPP include antibiotics that ameliorate infection and voiding complications. Anti-inflammatories and alphablockers can also be utilized. Neurologic treatments include the use of neuropathic pain drugs for instance pregabalin, gabapentin, and amitriptyline. Acupuncture, lifestyle changes, physical therapy, shockwave therapy, prostatic massage, and trigger point release are nonpharmacological treatments. Pelvic floor physical therapy comprises of biofeedback, nerve gliding, internal myofascial release, manual therapy, muscle control exercises, muscle energy, acupressure, and mobilization techniques.

Accordingly, there is need to treat the underlying myofascial pain syndrome and neurogenic pain seen in CPP patients, preferably via an outpatient neuromuscular protocol.

SUMMARY

Neuromuscular dysfunction in patients with chronic pelvic pain can be treated with anesthetic injections to the levator ani sling muscles (to reduce muscle spasticity) and high volume pudendal and posterior femoral cutaneous nerve blocks (to both reduce neurogenic inflammation and mechanically open the space so the nerves can flow freely with less restriction and more blood flow). Additionally, to treat the peripheral and central sensitization found in chronic pelvic pain patients, embodiments of the disclosed treatment also include high volume nerve blocks of the ilioinguinal, genitofemoral, pudendal, and/or perineal nerves.

BRIEF DESCRIPTION OF THE DRAWING

Aspects of exemplary embodiments may be better understood with reference to the accompanying drawings. The components in the drawings are not necessarily to scale, emphasis instead being placed upon illustrating the principles of exemplary embodiments.

FIG. 1 is a graph showing the percentage of patients (receiving embodiments of the disclosed treatment and a prior art treatment) who reported each improvement in pain assessment using the visual analog scale (VAS).

DETAILED DESCRIPTION

Disclosed are embodiments of a treatment for neuromuscular dysfunction in patients experiencing chronic pelvic pain. In some embodiments, the treatment may include administration of an anesthetic and a steroid. While this disclosure may refer to a specific anesthetic (i.e., lidocaine 1%), those of ordinary skill in the art will recognize other anesthetics (e.g., bupivacaine and/or Marcaine) may also be clinically effective and preferred for certain patients for a variety of reasons (e.g., allergic reaction, longer action duration, etc.). Similarly, while this disclosure may refer to a specific steroid (i.e., dexamethasone), those of ordinary skill in the art will recognize other steroids (e.g., kenolog) may also be clinically effective and preferred for certain patients for a variety of reasons. Additionally, as described in detail below, peripheral nerve blocks may be administered using normal saline (rather than a steroid) to obtain the mechanical benefits described below without the deleterious effects of excessive steroid use.

Additionally, while this disclosure may refer to examples of specific dosage amounts, those of ordinary skill in the art will recognize that similar dosage amounts may be similarly effective. Accordingly, as used herein:

"2 milliliters" or "2 ml" means "at least 1 ml, preferably at least 1.5 ml, more preferably at least 1.7 ml, even more preferably at least 1.9 ml";

"3 milliliters" or "3 ml" means "at least 2 ml, preferably at least 2.5 ml, more preferably at least 2.7 ml, even more preferably at least 2.9 ml";

"5 milliliters" or "5 ml" means "at least 4 ml, preferably at least 4.5 ml, more preferably at least 4.7 ml, even more preferably at least 4.9 ml"; and "7 cubic centimeters" or "7 cc" means "at least 6 cc, preferably at least 6.5 cc, more preferably at least 6.7 cc, even more preferably at least 6.9 cc".

The disclosed treatment method includes a series of ultrasound guided trigger point injections of an anesthetic (e.g., 1 cubic centimeter (cc) of lidocaine 1%) to each of the six muscles of the levator ani sling (the left and right iliococcygeus, the left and right pubococcygeus, and the left and right puborectalis) and an ultrasound-guided bilateral ilioinguinal nerve block. In preferred embodiments, the bilateral ilioinguinal nerve block is performed by administering an anesthetic and a steroid (e.g., 5 ml of lidocaine 1% and 2 ml of dexamethasone) to each of the left and right ilioinguinal nerves. In some embodiments, the treatment method also includes a bilateral genitofemoral nerve block performed by administering an anesthetic and a steroid (e.g., 3 ml of lidocaine 1% and 2 ml of dexamethasone to each of the left and right genitofemoral nerves).

In preferred embodiments, an ultrasound guided pudendal nerve block is performed with each trigger point injection on the same side as the trigger point injection. Each pudendal nerve block may be performed by administering an anesthetic (e.g., 7 cc of lidocaine 1%). In preferred embodiments, 2 ml of a steroid (e.g., dexamethasone) is also administered during the first two pudendal nerve blocks and 2 ml of normal saline is also administered during the subsequent pudendal nerve blocks.

In preferred embodiments, each trigger point injection is administered simultaneously with a pudendal nerve block on the same side as the injection. For instance, using ultrasound guidance, the pudendal nerve block may be administered using a needle that is then redirected to administer the injection before being completely retracted from the patient. Accordingly, for each simultaneous trigger point injection and pudendal nerve block, the patient only needs to be punctured once.

In preferred embodiments, each pudendal nerve block is followed by an ultrasound guided posterior femoral cutaneous nerve block on the same side as the trigger point injection. In preferred embodiments, the posterior femoral cutaneous nerve block is performed by administering an anesthetic and a steroid (e.g., 5 ml of lidocaine 1% and 2 ml of dexamethasone).

In some embodiments, the treatment may also include perineal nerve blocks administered to each of the left and right perineal nerves. In preferred embodiments, each perineal nerve block is performed by administering an anesthetic and a steroid (e.g., 5 ml of lidocaine 1% and 2 ml of dexamethasone). In some embodiments, the perineal nerve blocks may be administered during treatment sessions when non-steroidal pudendal nerve blocks (i.e., using normal saline) are administered on the same side (e.g., in weeks 3 and 4 or weeks 5 and 6).

In some embodiments, the treatment may also include dorsal nerve blocks administered to each of the left and right dorsal nerves. In preferred embodiments, each dorsal nerve block is performed by administering an anesthetic and a steroid (e.g., 3 ml of lidocaine 1% and 2 ml of dexamethasone). In some embodiments, the dorsal nerve blocks may be administered during treatment sessions when non-steroidal pudendal nerve blocks (i.e., using normal saline) are administered on the same side (e.g., in weeks 3 and 4 or weeks 5 and 6).

In various embodiments, each ultrasound-guided peripheral posterior femoral cutaneous nerve block may be administered using ultrasound settings that include a pediatric abdomen preset, a depth of 10 cm, a mode of color doppler, and/or a color gain of 40-50%; each pudendal nerve block may be administered using ultrasound settings that include an abdomen preset, a depth of 12 centimeters (cm), a mode of color doppler, and/or a color gain of 40-50%; and the bilateral ilioinguinal nerve block may be administered using ultrasound settings that include a nerve preset, a depth of 5 cm, a mode of color doppler, and/or a color gain of 40-50%.

The trigger point injections may be administered with a 27-gauge needle. A topical anesthetic spray may be applied before each injection. Patients may be pre-medicated (for example, with diclofenac 75 mg by mouth) before each injection. Patients may sit on ice for 10 minutes before resuming normal activities.

Throughout the treatment, patients may also receive pelvic floor physical therapy (e.g., internal release of the pelvic floor hypertonic musculature, visceral mobilization, scar tissue mobilization, skin rolling along the lower abdomen and buttocks, nerve gliding along the pudendal and posterior femoral cutaneous nerves, diaphragmatic breathing, etc.).

Patients with chronic pelvic pain syndrome experience pelvic muscles that are short, spastic and weaker. The pelvic muscles cause neural ischemia in which the pelvic muscles clamp down on the pelvic nerves, limiting blood flow through the pelvic nerves. That neural ischemia is most prevalent in the pudendal nerves and the posterior femoral cutaneous nerves and may also be found in the perineal nerves, the dorsal nerves, etc.

The disclosed treatment provides several clinical benefits that are particularly effective in combination. The trigger point injections treat the muscles so they are long, lean, open, less spastic, and less clamped down on the pelvic nerves while the peripheral nerve blocks reduce neurogenic inflammation. Additionally, the peripheral nerve blocks in the disclosed embodiments are higher volume than is typically administered, providing a mechanical benefit. The higher-volume peripheral nerve blocks (e.g., 7 ml of lidocaine 1% and 2 ml of either dexamethasone or normal saline administered to the pudendal nerves) open up the space where the pelvic nerves can flow freely with less restriction and more blood flow. In specific preferred embodiments, one administration of steroid (e.g., dexamethasone) to each of the left and right pudendal nerves is sufficiently effective to reduce neurogenic inflammation while subsequent administration of normal saline provides the mechanical benefit above without the deleterious effects of excessive steroid use.

The efficacy of anesthetic injections to the levator ani sling combined with peripheral nerve blocks of the pudendal and posterior femoral cutaneous nerves have been shown in Natarajan et al.[1] The treatment protocol described in Natarajan et al., however, is limited in that it fails to address any neurological disfunction that may exist in other pelvic nerves of chronic pelvic pain patients. Accordingly, various disclosed embodiments include additional features that have been shown to significantly improve clinical outcomes relative to the treatment protocol described in Natarajan et al.

[1] Natarajan, J., Ahmed, T., Patil, S., Mamsaang, M., Kapadia, R., Tailor, Y., & Shrikhande, A. (2021). Pain and functionality improved when underlying neuromuscular dysfunction addressed in chronic pelvic pain patients. Neurourology and urodynamics, 40(6), 1609-1615. https://doi.org/10.1002/nau.24726

Most significantly, preferred embodiments further include a high volume bilateral ilioinguinal nerve block performed by administering an anesthetic and a steroid (e.g., 5 ml of lidocaine 1% and 2 ml of dexamethasone to each of the left and right ilioinguinal nerve). As shown in Table 1 below, chronic pelvic pain patients who received a bilateral ilioinguinal nerve block were found to have a lower minimum pain assessment at 3 or 6 month follow-up visits than those who received the treatment protocol described in Natarajan et al.

TABLE 1

| Visual Analog Scale (VAS) | Without bilateral ilioinguinal nerve block | With bilateral ilioinguinal nerve block |
|---|---|---|
| Average Patient VAS Score at Neutral Position | 7.11 | 6.38 |
| Average VAS Score at Follow Up (Minimum 3 or 6 months) | 3.70 | 2.79 |
| Average Improvement (VAS Score) | 3.40 | 3.60 |
| Average Improvement (VAS Score %) | 48% | 56% |

FIG. 1 is a graph showing the percentage of patients who reported each improvement in pain assessment using the visual analog scale (VAS). Specifically, a positive number (e.g., 1) represents a reduced pain assessment (e.g., from 6 to 5) while a 0 represents no improvement and a negative number represents an increased pain assessment. As shown in FIG. 1, larger percentages of patients who received bilateral ilioinguinal nerve blocks reported higher improvements in pain assessments.

Additionally, for patients diagnosed with neurogenic inflammation in those nerves, the disclosed treatment may also include a bilateral genitofemoral nerve block and/or pudendal or dorsal nerve blocks.

In contrast to the treatment protocol described in Natarajan et al., the disclosed embodiments recognize that chronic pain is different than acute pain in that neuromuscular disfunction spreads to through the peripheral nervous system (and, ultimately, the central nervous system). More specifically, peripheral and central sensitization causes aberrant firing of the nerves to spread to other pelvic nerves (and to the spinal cord, and, ultimately, the brain). Accordingly, failing to treat other pelvic nerves (in particular, the upper third of the pelvis) ignores a large innervation in the pelvis and does allow for a complete resolution of chronic pelvic pain symptoms.

EXAMPLES

The following non-limiting examples provide those of ordinary skill in the art with specific preferred methods to treat neuromuscular dysfunction in chronic pelvic pain patients within the scope of the present disclosure and are not intended to limit the scope of the invention.

Example 1—A Bilateral Ilioinguinal Nerve Block Combined with Six Anesthetic Injections to the Levator Ani Sling and Pudendal and Posterior Femoral Cutaneous Nerve Blocks Week 1: The patient may be pre-medicated (for example, with diclofenac 75 mg by mouth). With the patient lying in a prone position, an ultrasound guided, high volume, steroidal pudendal nerve block (e.g., 7 ml of lidocaine 1% and 2 ml of dexamethasone) is administered on a first side (left or right) followed by a trigger point injection (e.g., 1 cubic centimeter (cc) of lidocaine 1%) to a first of the three muscles of the levator ani sling (the iliococcygeus muscle, the pubococcygeus muscle, or the puborectalis muscle) on the first side. The patient is then flipped to a supine position and an ultrasound-guided posterior femoral cutaneous nerve block (e.g., 5 ml of lidocaine 1% and 2 ml of dexamethasone) is administered 4 cm inferior to the ischial tuberosity on the first side. The patient may be advised to sit on ice for 10 minutes before resuming normal activities.

Week 2: The patient may be pre-medicated (for example, with diclofenac 75 mg by mouth). With the patient lying in the prone position, the ultrasound guided, high volume, steroidal pudendal nerve block is administered on the opposite side (right or left) followed by the trigger point injection to the first of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 3: The patient may be pre-medicated (for example, with diclofenac 75 mg by mouth). With the patient lying in the prone position, the ultrasound guided, high volume, steroid-free pudendal nerve block (e.g., 7 ml of lidocaine 1% and 2 ml of normal saline) is administered on the first side followed by the trigger point injection to a second of the three muscles of the levator ani sling on the first side. The patient is then flipped to the supine position and the ultrasound-guided posterior femoral cutaneous nerve block is administered 4 cm inferior to the ischial tuberosity on the first side. The patient may be advised to sit on ice for 10 minutes before resuming normal activities.

Week 4: The patient may be pre-medicated (for example, with diclofenac 75 mg by mouth). With the patient lying in the prone position, the ultrasound guided, high volume, steroid-free pudendal nerve block administered on the opposite side followed by the trigger point injection to the second of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 5: The patient may be pre-medicated (for example, with diclofenac 75 mg by mouth). With the patient lying in the prone position, the ultrasound guided, high volume, steroid-free pudendal nerve block is administered on the first side followed by the trigger point injection to the third of the three muscles of the levator ani sling on the first side. The patient is then flipped to the supine position and the ultrasound-guided posterior femoral cutaneous nerve block is administered 4 cm inferior to the ischial tuberosity on the first side. The patient may be advised to sit on ice for 10 minutes before resuming normal activities.

Week 6: The patient may be pre-medicated (for example, with diclofenac 75 mg by mouth). With the patient lying in the prone position, the ultrasound guided, high volume, steroid-free pudendal nerve block administered on the opposite side followed by the trigger point injection to the third of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 7: The patient may be pre-medicated (for example, with diclofenac 75 mg by mouth). With the patient in the supine position, an ultrasound guided, high volume, bilateral ilioinguinal nerve block is administered (e.g., 5 ml of lidocaine 1% and 2 ml of dexamethasone to each of the left and right ilioinguinal nerves). The patient may be advised to sit on ice for 10 minutes before resuming normal activities.

Example 2—Bilateral Ilioinguinal and Genitofemoral Nerve Blocks Combined with Six Anesthetic Levator Ani Sling Injections and Pudendal and PFCN Nerve Blocks Week 1: The patient may be pre-medicated (for example, with diclofenac 75 mg by mouth). With the patient lying in a prone position, an ultrasound guided, high volume, steroidal pudendal nerve block (e.g., 7 ml of lidocaine 1% and 2 ml of dexamethasone) is administered on a first side (left or right) followed by a trigger point injection (e.g., 1 cubic centimeter (cc) of lidocaine 1%) to a first of the three muscles of the levator ani sling (the iliococcygeus muscle, the pubococcygeus muscle, or the puborectalis muscle) on the first side. The patient is then flipped to a supine position and an ultrasound-guided posterior femoral cutaneous nerve block (e.g., 5 ml of lidocaine 1% and 2 ml of dexamethasone) is administered 4 cm inferior to the ischial tuberosity on the first side. The patient may be advised to sit on ice for 10 minutes before resuming normal activities.

Week 2: The patient may be pre-medicated (for example, with diclofenac 75 mg by mouth). With the patient lying in the prone position, the ultrasound guided, high volume, steroidal pudendal nerve block is administered on the opposite side (right or left) followed by the trigger point injection to the first of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 3: The patient may be pre-medicated (for example, with diclofenac 75 mg by mouth). With the patient lying in the prone position, the ultrasound guided, high volume, steroid-free pudendal nerve block (e.g., 7 ml of lidocaine 1% and 2 ml of normal saline) is administered on the first side followed by the trigger point injection to a second of the three muscles of the levator ani sling on the first side. The patient is then flipped to the supine position and the ultrasound-guided posterior femoral cutaneous nerve block is administered on the first side. The patient may be advised to sit on ice for 10 minutes before resuming normal activities.

Week 4: The patient may be pre-medicated (for example, with diclofenac 75 mg by mouth). With the patient lying in the prone position, the ultrasound guided, high volume, steroid-free pudendal nerve block administered on the opposite side followed by the trigger point injection to the second of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 5: The patient may be pre-medicated (for example, with diclofenac 75 mg by mouth). With the patient lying in the prone position, the ultrasound guided, high volume, steroid-free pudendal nerve block is administered on the first side followed by the trigger point injection to the third of the three muscles of the levator ani sling on the first side. The patient is then flipped to the supine position and the ultrasound-guided posterior femoral cutaneous nerve block is administered on the first side. The patient may be advised to sit on ice for 10 minutes before resuming normal activities.

Week 6: The patient may be pre-medicated (for example, with diclofenac 75 mg by mouth). With the patient lying in the prone position, the ultrasound guided, high volume, steroid-free pudendal nerve block administered on the opposite side followed by the trigger point injection to the third of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 7: The patient may be pre-medicated (for example, with diclofenac 75 mg by mouth). With the patient in the supine position, an ultrasound guided, high volume, bilateral ilioinguinal nerve block (e.g., 5 ml of lidocaine 1% and 2 ml of dexamethasone to each of the left and right ilioinguinal nerves) and bilateral genitofemoral nerve block (e.g., 3 ml of lidocaine 1% and 2 ml of dexamethasone to each of the left and right genitofemoral nerves) are administered. The patient may be advised to sit on ice for 10 minutes before resuming normal activities.

Example 3—Perineal Nerve Blocks with Six Anesthetic Levator Ani Sling Injections and Pudendal and Posterior Femoral Cutaneous Nerve Blocks Week 1: The patient may be pre-medicated (for example, with diclofenac 75 mg by mouth). With the patient lying in a prone position, an ultrasound guided, high volume, steroidal pudendal nerve block (e.g., 7 ml of lidocaine 1% and 2 ml of dexamethasone) is administered on a first side (left or right) along with a trigger point injection (e.g., 1 cubic centimeter (cc) of lidocaine 1%) to a first of the three muscles of the levator ani sling (the iliococcygeus muscle, the pubococcygeus muscle, or the puborectalis muscle) on the first side. The patient is then flipped to a supine position and an ultrasound-guided posterior femoral cutaneous nerve block (e.g., 5 ml of lidocaine 1% and 2 ml of dexamethasone) is administered 4 cm inferior to the ischial tuberosity on the first side. The patient may be advised to sit on ice for 10 minutes before resuming normal activities.

Week 2: The patient may be pre-medicated (for example, with diclofenac 75 mg by mouth). With the patient lying in the prone position, the ultrasound guided, high volume, steroidal pudendal nerve block is administered on the opposite side (right or left) along with the trigger point injection to the first of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 3: The patient may be pre-medicated (for example, with diclofenac 75 mg by mouth). With the patient lying in the prone position, the ultrasound guided, high volume, steroid-free pudendal nerve block (e.g., 7 ml of lidocaine 1% and 2 ml of normal saline) is administered on the first side along with along with a perineal nerve block (e.g., 5 ml of lidocaine 1% and 2 ml of dexamethasone) on the first side and the trigger point injection to a second of the three muscles of the levator ani sling on the first side. The patient is then flipped to the supine position and the ultrasound-guided posterior femoral cutaneous nerve block is administered on the first side. The patient may be advised to sit on ice for 10 minutes before resuming normal activities.

Week 4: The patient may be pre-medicated (for example, with diclofenac 75 mg by mouth). With the patient lying in the prone position, the ultrasound guided, high volume, steroid-free pudendal nerve block administered on the opposite side along with the perineal nerve block on the opposite side and the trigger point injection to the second of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 5: The patient may be pre-medicated (for example, with diclofenac 75 mg by mouth). With the patient lying in the prone position, the ultrasound guided, high volume, steroid-free pudendal nerve block is administered on the first side along with and the trigger point injection to the third of the three muscles of the levator ani sling on the first side. The patient is then flipped to the supine position and the ultrasound-guided posterior femoral cutaneous nerve block is administered on the first side. The patient may be advised to sit on ice for 10 minutes before resuming normal activities.

Week 6: The patient may be pre-medicated (for example, with diclofenac 75 mg by mouth). With the patient lying in the prone position, the ultrasound guided, high volume, steroid-free pudendal nerve block administered on the opposite side along with the trigger point injection to the third of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 7: The patient may be pre-medicated (for example, with diclofenac 75 mg by mouth). With the patient in the supine position, an ultrasound guided, high volume, bilateral ilioinguinal nerve block is administered (e.g., 5 ml of lidocaine 1% and 2 ml of dexamethasone to each of the left and right ilioinguinal nerves). The patient may be advised to sit on ice for 10 minutes before resuming normal activities.

Example 4—Dorsal Nerve Blocks with Six Anesthetic Levator Ani Sling Injections and Pudendal and Posterior Femoral Cutaneous Nerve Blocks Week 1: The patient may be pre-medicated (for example, with diclofenac 75 mg by mouth). With the patient lying in a prone position, an ultrasound guided, high volume, steroidal pudendal nerve block (e.g., 7 ml of lidocaine 1% and 2 ml of dexamethasone) is administered on a first side (left or right) along with a trigger point injection (e.g., 1 cubic centimeter (cc) of lidocaine 1%) to a first of the three muscles of the levator ani sling (the iliococcygeus muscle, the pubococcygeus muscle, or the puborectalis muscle) on the first side. The patient is then flipped to a supine position and an ultrasound-guided posterior femoral cutaneous nerve block (e.g., 5 ml of lidocaine 1% and 2 ml of dexamethasone) is administered 4 cm inferior to the ischial tuberosity on the first side. The patient may be advised to sit on ice for 10 minutes before resuming normal activities.

Week 2: The patient may be pre-medicated (for example, with diclofenac 75 mg by mouth). With the patient lying in the prone position, the ultrasound guided, high volume, steroidal pudendal nerve block is administered on the opposite side (right or left) along with the trigger point injection to the first of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 3: The patient may be pre-medicated (for example, with diclofenac 75 mg by mouth). With the patient lying in the prone position, the ultrasound guided, high volume, steroid-free pudendal nerve block (e.g., 7 ml of lidocaine 1% and 2 ml of normal saline) is administered on the first side along with the trigger point injection to a second of the three muscles of the levator ani sling on the first side. The patient is then flipped to the supine position and the ultrasound-guided posterior femoral cutaneous nerve block and a dorsal nerve block (e.g., 3 ml of lidocaine 1% and 2 ml of dexamethasone) are administered on the first side. The patient may be advised to sit on ice for 10 minutes before resuming normal activities.

Week 4: The patient may be pre-medicated (for example, with diclofenac 75 mg by mouth). With the patient lying in the prone position, the ultrasound guided, high volume, steroid-free pudendal nerve block administered on the opposite side along with the trigger point injection to the second of the three muscles of the levator ani sling on the opposite side. The patient is then flipped to the supine position and the ultrasound-guided posterior femoral cutaneous nerve block and dorsal nerve block are administered on the opposite side. The patient may be advised to sit on ice for 10 minutes before resuming normal activities.

Week 5: The patient may be pre-medicated (for example, with diclofenac 75 mg by mouth). With the patient lying in the prone position, the ultrasound guided, high volume, steroid-free pudendal nerve block is administered on the first side along with the trigger point injection to the third of the three muscles of the levator ani sling on the first side. The patient is then flipped to the supine position and the ultrasound-guided posterior femoral cutaneous nerve block is administered on the first side. The patient may be advised to sit on ice for 10 minutes before resuming normal activities.

Week 6: The patient may be pre-medicated (for example, with diclofenac 75 mg by mouth). With the patient lying in the prone position, the ultrasound guided, high volume, steroid-free pudendal nerve block administered on the opposite side along with the trigger point injection to the third of the three muscles of the levator ani sling on the opposite side. The patient is then flipped to the supine position and the ultrasound-guided posterior femoral cutaneous nerve block is administered on the opposite side. The patient may be advised to sit on ice for 10 minutes before resuming normal activities.

Week 7: The patient may be pre-medicated (for example, with diclofenac 75 mg by mouth). With the patient in the supine position, an ultrasound guided, high volume, bilateral ilioinguinal nerve block is administered (e.g., 5 ml of lidocaine 1% and 2 ml of dexamethasone to each of the left and right ilioinguinal nerves). The patient may be advised to sit on ice for 10 minutes before resuming normal activities.

While preferred embodiments have been described above, those skilled in the art who have reviewed the present disclosure will readily appreciate that other embodiments can be realized within the scope of the invention. Accordingly, the present invention should be construed as limited only by any appended claims.

What is claimed is:

1. A method for treating pelvic pain, the method comprising:
    performing, using ultrasound guidance, a first pudendal nerve block of a left pudendal nerve by injecting a first anesthetic volume;
    performing, following the first pudendal nerve block of the left pudendal nerve, and using ultrasound guidance, an injection to a left iliococcygeus muscle;
    performing, using ultrasound guidance, a first pudendal nerve block of a right pudendal nerve by injecting a second anesthetic volume;
    performing, following the first pudendal nerve block of the right pudendal nerve, and using ultrasound guidance, an injection to a right iliococcygeus muscle;
    performing, using ultrasound guidance, a second pudendal nerve block of the left pudendal nerve by injecting a third anesthetic volume;
    performing, following the second pudendal nerve block of the left pudendal nerve, and using ultrasound guidance, an injection to a left pubococcygeus muscle;
    performing, using ultrasound guidance, a second pudendal nerve block of the right pudendal nerve by injecting a fourth anesthetic volume;
    performing, following the second pudendal nerve block of the right pudendal nerve, and using ultrasound guidance, an injection to a right pubococcygeus muscle;
    performing, using ultrasound guidance, a third pudendal nerve block of the left pudendal nerve by injecting a fifth anesthetic volume;
    performing, following the third pudendal nerve block of the left pudendal nerve, and using ultrasound guidance, an injection to a left puborectalis muscle;
    performing, using ultrasound guidance, a third pudendal nerve block of the right pudendal nerve by injecting a sixth anesthetic volume;
    performing, following the third pudendal nerve block of the right pudendal nerve, and using ultrasound guidance, an injection to a right puborectalis muscle; and
    performing, using ultrasound guidance, a bilateral ilioinguinal nerve block.

2. The method of claim 1, wherein performing the bilateral ilioinguinal nerve block comprises injecting lidocaine and dexamethasone.

3. The method of claim 2, wherein injecting the lidocaine and the dexamethasone comprises injecting 5 milliliters (ml) of the lidocaine 1% and 2 ml of the dexamethasone to each of a left ilioinguinal nerve and a right ilioinguinal nerve.

4. The method of claim 1, wherein performing the bilateral ilioinguinal nerve block further comprises:
performing a bilateral genitofemoral nerve block.

5. The method of claim 4, wherein performing the bilateral genitofemoral nerve block comprises injecting lidocaine and dexamethasone.

6. The method of claim 5, wherein injecting the lidocaine and the dexamethasone comprises injecting 3 ml of the lidocaine 1% and 2 ml of the dexamethasone to each of a left genitofemoral nerve and a right genitofemoral nerve.

7. The method of claim 1, further comprising:
performing a perineal nerve block of each of a left perineal nerve and a right perineal nerve.

8. The method of claim 7, wherein performing the perineal nerve block of each of the left perineal nerve and the right perineal nerve comprises injecting lidocaine and dexamethasone.

9. The method of claim 8, wherein injecting the lidocaine and the dexamethasone comprises injecting 5 ml of the lidocaine 1% and 2 ml of the dexamethasone.

10. The method of claim 1, further comprising:
performing a dorsal nerve block of each of a left perineal nerve and a right perineal nerve.

11. The method of claim 10, wherein performing the dorsal nerve block of each of the left perineal nerve and the right perineal nerve comprises injecting lidocaine and dexamethasone.

12. The method of claim 11, wherein injecting the lidocaine and the dexamethasone comprises injecting 3 ml of the lidocaine 1% and 2 ml of the dexamethasone.

13. The method of claim 1, wherein each of the injection to the left iliococcygeus muscle, the injection to the right iliococcygeus muscle, the injection to the left pubococcygeus muscle, the injection to the right pubococcygeus muscle, the injection to the left puborectalis muscle, and the injection to the right puborectalis muscle is performed by injecting an anesthetic.

14. The method of claim 13, wherein the anesthetic comprises lidocaine.

15. The method of claim 14, wherein the lidocaine comprises 1 cubic centimeter (cc) of lidocaine 1%.

16. The method of claim 1, wherein the first anesthetic volume and the second anesthetic volume are the same.

17. The method of claim 1, wherein the first anesthetic volume and the second anesthetic volume comprise lidocaine and dexamethasone.

18. The method of claim 17, wherein the lidocaine and the dexamethasone comprise 7 ml of lidocaine 1% and 2 ml of dexamethasone.

19. The method of claim 1, wherein the third anesthetic volume, the fourth anesthetic volume, the fifth anesthetic volume, and the sixth anesthetic volume are the same.

20. The method of claim 1, wherein the third anesthetic volume, the fourth anesthetic volume, the fifth anesthetic volume, and the sixth anesthetic volume comprise lidocaine.

21. The method of claim 20, wherein the lidocaine comprises 7 ml of lidocaine 1% and 2 ml of normal saline.

22. The method of claim 1, wherein:
the injection to the left iliococcygeus muscle is performed by redirecting a needle used to inject the first anesthetic volume to perform the first pudendal nerve block of the left pudendal nerve;
the injection to the right iliococcygeus muscle is performed by redirecting a needle used to inject the second anesthetic volume to perform the first pudendal nerve block of the right pudendal nerve;
the injection to the left pubococcygeus muscle is performed by redirecting a needle used to inject the third anesthetic volume to perform the second pudendal nerve block of the left pudendal nerve;
the injection to the right pubococcygeus muscle is performed by redirecting a needle used to inject the fourth anesthetic volume to perform the second pudendal nerve block of the right pudendal nerve;
the injection to the left puborectalis muscle is performed by redirecting a needle used to inject the fifth anesthetic volume to perform the third pudendal nerve block of the left pudendal nerve; and
the injection to the right puborectalis muscle is performed by redirecting a needle used to inject the sixth anesthetic volume to perform the third pudendal nerve block of the right pudendal nerve.

23. The method of claim 1, further comprising:
performing, using ultrasound guidance, a posterior femoral cutaneous nerve block before each of the injection to the left iliococcygeus muscle, the injection to the right iliococcygeus muscle, the injection to the left pubococcygeus muscle, the injection to the right pubococcygeus muscle, the injection to the left puborectalis muscle, and the injection to the right puborectalis muscle is performed.

24. The method of claim 23, wherein each posterior femoral cutaneous nerve block is administered using ultrasound settings that include a pediatric abdomen preset, a depth of 10 centimeters (cm), a mode of color doppler, and/or a color gain of 40-50%.

25. The method of claim 1, wherein each of the first, the second, and the third pudendal nerve block of the left pudendal nerve and the first, the second, and the third pudendal nerve block of the right pudendal nerve is performed using ultrasound settings that include an abdomen preset, a depth of 12 centimeters (cm), a mode of color doppler, and/or a color gain of 40-50%.

26. The method of claim 1, wherein the bilateral ilioinguinal nerve block is administered using ultrasound settings that include a nerve preset, a depth of 5 centimeters (cm), a mode of color doppler, and/or a color gain of 40-50%.

27. The method of claim 1, wherein the first pudendal nerve block of the left pudendal nerve by injecting the first anesthetic volume is performed using a first needle and the injection to the left iliococcygeus muscle is performed using the first needle without removing the first needle.

28. The method of claim 1, wherein each of the injection to the left iliococcygeus muscle, the injection to the right iliococcygeus muscle, the injection to the left pubococcygeus muscle, the injection to the right pubococcygeus muscle, the injection to the left puborectalis muscle, and the injection to the right puborectalis muscle is performed using a 27-gauge needle.

29. The method of claim 1, further comprising applying a topical anesthetic spray before each pudendal nerve block is performed.

30. The method of claim 1, wherein treating the pelvic pain comprises treating pelvic floor hypertonic musculature.

* * * * *